Nov. 2, 1954 R. O. RUBEL, JR Plant Pat. 1,312
CAMELLIA PLANT
Filed Sept. 15, 1953
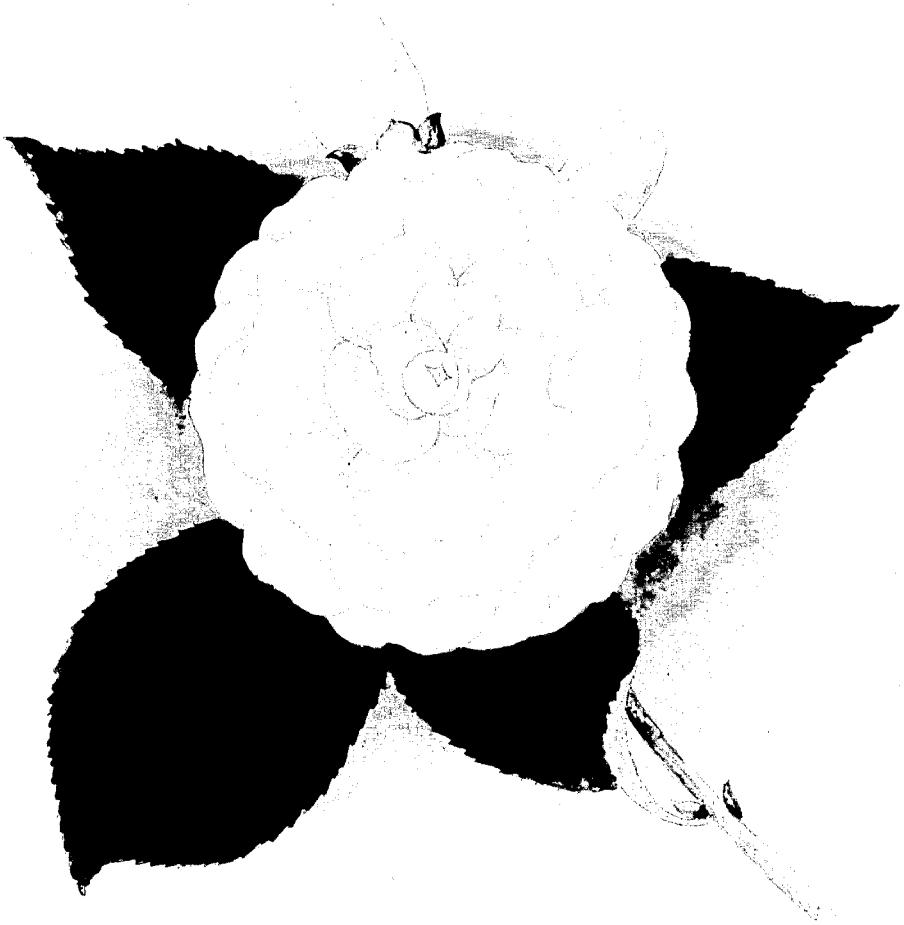
WITNESS
Addison E. Avery
INVENTOR
ROBERT O. RUBEL, JR.
by Ramondler Lumnler & Snow,
ATTYS.

United States Patent Office

Plant Pat. 1,312
Patented Nov. 2, 1954

1,312

CAMELLIA PLANT

Robert O. Rubel, Jr., Mobile, Ala., assignor to Cliff Harris, Mobile, Ala.

Application September 15, 1953, Serial No. 380,386

1 Claim. (Cl. 47—60)

This invention relates to a new and distinctive variety of camellia plant which originated in 1927 in my garden as a seedling obtained as a result of systematic harvesting and growing of seed from selected well-known varieties of camellias.

The plant has been asexually reproduced by cuttings and graftings at Mobile, Alabama, and has been found to come normally true with unicolored light rose pink petals; but some plants have produced sport blooms of variegated colors of pink with white variegations.

The plant is identical in form and has the same number of petals as Alba Plena (unpatented), usually 100 petals, but it differs therefrom in its distinctive coloring. It is a stronger and more vigorous grower than Alba Plena which it resembles except for color.

It has exceptional keeping qualities as a corsage flower and is excellent for use as a florist's cut flower. At Mobile, Alabama, it flowers out of doors as early as October and continues blooming through March. It has bloomed after and during freezing weather, growing outside unprotected.

The accompanying painting shows this new camellia in its natural colors, including flower and foliage.

The following is a detailed description of my new variety:

Parentage: Seedling. Seed parent known.

Classification: *Camellia japonica.* Reproduced asexually from cuttings and grafting.

Flower: Large and unicolored light rose pink, occasionally producing white variegations.

*Borne.*—Singly and double.

*Size.*—4 to 4¾ in. (10–12 cm.) and larger in diameter and 1 3/16 in. (3 cm.) high.

*Shaped.*—Flat.

*Petalage.*—100 petals, outer petals 2 in. (5 cm.) long and 1⅜ in. (3.5 cm.) wide. Form—orbicular, attenuate at base, imbricated. Texture—soft. Appearance—satiny.

Affected by hot weather, 60° or above.

Lasting quality excellent on plant and as a cut flower.

Bud:

*Form.*—Elliptic ovoid—full imbricated double.

*Size.*—Medium, 1 in. (2.5 cm.) long x ¾ in. (1.8 cm.) in diameter.

*Sepals.*—8 in number, partially hooded over bud.

*Color.*—Medium green until pink of petals is displayed. Outer sepals turn brownish green just before flowering.

Calyx: Cup-shaped, medium sized, 1 in. (2.5 cm.) across. Does not split. Aspect is smooth.

Genital organs: None.

Plant:

*Form.*—Round.

*Height.*—Depends on age of plant. Growth is compact, vigorous and branching.

Foliage: Abundant in quantity.

*Size of leaves.*—3 3/16 in.—4¾ in. (8–12 cm.) long x 2–2⅝ in. (5–6.5 cm.) wide.

*Form.*—Ovate, bases cuneate, apexes acute, finely serrated.

*Texture.*—Coriaceous.

*Color.*—Upper side, dark green. Under side, light green.

*Petioles.*—Approximately ⅜ to ¾ in. (1–2 cm.) dark green in color.

The color designations, according to "A Dictionary of Color by Maerz and Paul" are as follows:

| Flower | Plate | Ltr. | No. |
|---|---|---|---|
| Lightest shade | 50 | J | 6. |
| shading into | 50 | I | 5. |
| Leaves: | | | |
| Fine serrated edge—pointed leaf— | | | |
| Top of leaf | 22 | L | 7 plus yellow. |
| Under side of leaf | 21 | L | 6. |
| Stem | 7 | J | 11. |

I claim:

A new and distinct variety of *Camellia japonica* plant, characterized by its distinctive round unicolored light rose pink colored flowers, exceptional keeping qualities, and long blooming period, substantially as illustrated and described.

No references cited.